United States Patent [19]

Kumar

[11] Patent Number: 4,610,251
[45] Date of Patent: Sep. 9, 1986

[54] SURGICAL STAPLE

[76] Inventor: Sarbjeet S. Kumar, 514 Brown St., Springfield, Tenn. 37172

[21] Appl. No.: 724,837

[22] Filed: Apr. 19, 1985

[51] Int. Cl.$^4$ ............................................. A61B 17/04
[52] U.S. Cl. ................................ 128/334 R; 128/337; 411/460; 411/470
[58] Field of Search ............... 128/334 R, 334 C, 335, 128/336, 337; 411/457, 458, 459, 460, 470; D8/49, 50; 24/562

[56] References Cited

U.S. PATENT DOCUMENTS

| | | | |
|---|---|---|---|
| 1,728,316 | 9/1929 | Von Wachenfeldt | 128/334 R |
| 2,684,070 | 7/1954 | Kelsey | 128/337 |
| 3,214,810 | 11/1965 | Mathison | 128/337 |
| 4,014,492 | 3/1977 | Rothfoss | 227/19 |
| 4,317,451 | 3/1982 | Cerwin et al. | 128/337 |
| 4,489,875 | 12/1984 | Crawford et al. | 227/19 |

*Primary Examiner*—Gene Mancene
*Assistant Examiner*—John G. Weiss
*Attorney, Agent, or Firm*—Harrington A. Lackey

[57] ABSTRACT

A surgical staple for use in joining the opposed edges of an incision in the skin of a patient, in which the staple includes an elongated straight bridge portion, a pair of anchor prongs projecting in the same direction from the opposite ends of the bridge portion, and a pair of positioning prongs projecting toward each other from the opposite ends of the bridge portion at acute angles to, and in the same plane as, the anchor prongs. The surgical staple is adapted to be carried in the cartridge of a conventional surgical staple applicator and adapted to be deformed by the applicator to bend the bridge portion spanning the edges of the wound for emplacement of the opposed anchor and positioning prongs into the skin on opposite sides of the incision so that the positioning prongs urge the edges of the incision together, and all of the prongs prevent rotation of the staple relative to the incision.

7 Claims, 8 Drawing Figures

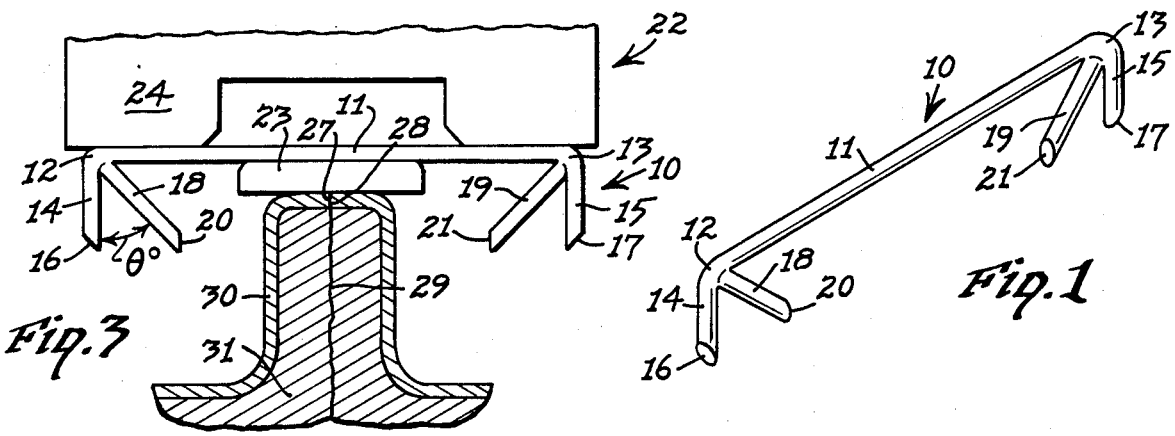
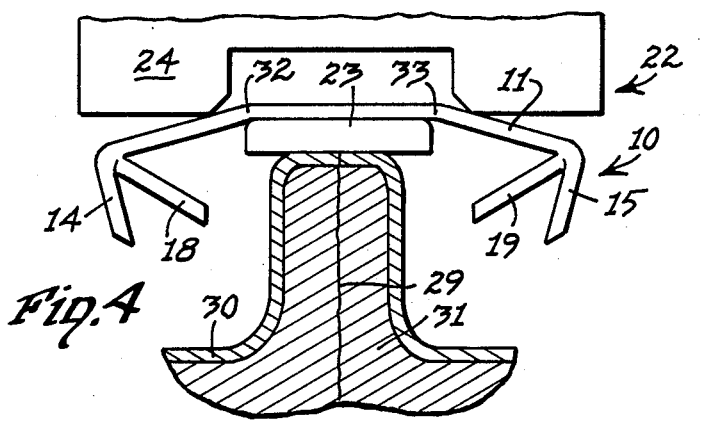
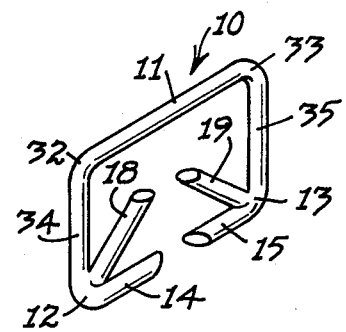
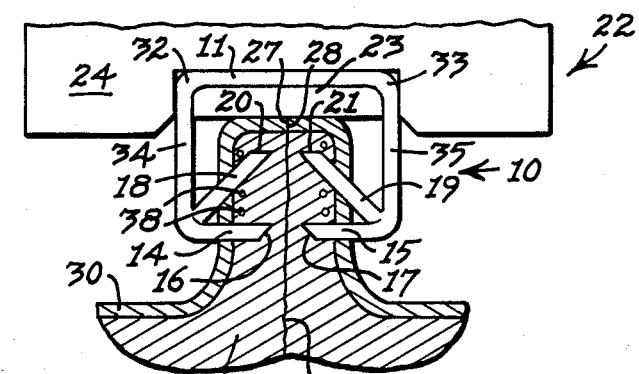
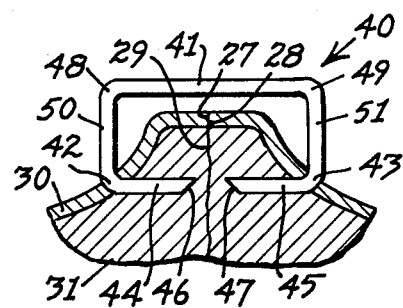
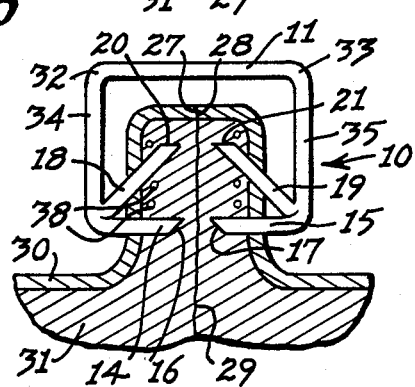
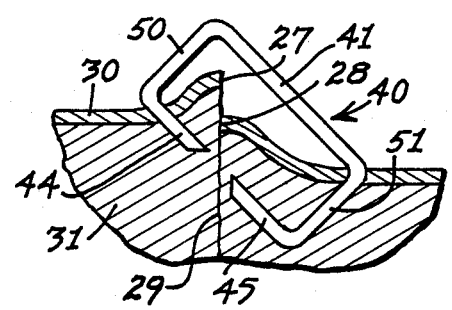

SURGICAL STAPLE

BACKGROUND OF THE INVENTION

This invention relates to a surgical staple, and more particularly to a surgical staple stabilized against rotation when emplaced transversely of the wound in a patient.

Surgical staples having an elongated straight central portion and a single pair of prongs depending from the opposite ends of the central portion, are well known in the art for closing wounds or incisions in the skin of a patient, as a rapid and effective substitute for suturing.

However, one important difficulty with the utilization of a conventional surgical staple having a single pair of terminal prongs is that the emplaced staple tends to rotate or tilt in a plane transverse to the length of the incision or wound. Accordingly, the lips or edges of the wound or incision are offset from each other, to increase the healing time and also to produce a relatively large scar. Moreover, the rotational attitude of the conventional surgical staple is more difficult to remove after the wound has healed than if the staple were not rotated.

Furthermore, where a conventional surgical staple is utilized to secure the edges of an incision or wound, there is the tendency of the wound edges to shift relative to each other causing pain to the patient, and producing some bleeding from the wound or incision.

One example of a modified surgical staple incorporating a pair of opposed prongs is disclosed in U.S. Pat. No. 4,014,492, of Rothfuss, issued Mar. 29, 1977.

The following U.S. patents disclose various types of clips, clamps and other devices for closing the opposed edges of cuts in the skin:

| | | |
|---|---|---|
| 2,421,193 | Gardner | May 27, 1947 |
| 2,472,009 | Gardner | May 31, 1949 |
| 2,669,747 | Detaranto | Feb. 23, 1954 |
| 2,910,067 | White | Oct. 27, 1959 |
| 3,068,869 | Shelden et al | Dec. 18, 1962 |
| 3,068,870 | Levin | Dec. 18, 1962 |
| 3,378,010 | Codling, et al | Apr. 16, 1968 |

Of the above patents, only the patents to Shelden et al, Levin and Codling et al, disclose wound or incision closing device having a pair of prongs on each side of the wound or incision, in which the prongs are spaced in a direction perpendicular to the length of the wound or incision. None of these devices disclose a surgical staple adapted to be utilized in a cartridge within a surgical staple applicator, nor do they address the unique problem of the rotation of surgical staples transversely of the wound or incision. U.S. Pat. No. 3,124,810 issued to Mathison on Nov. 2, 1965, entitled "FASTENER DEVICES" discloses a two-part fastener device for fabrics, such as diapers, including a flexible U-shaped fastener body having a plurality of opposed conical projections disposed angularly upward from the arms of the fastener body in closed position, and a closure cap member for compressing the arms together to join two pieces of fabric. When the closure cap member is removed from the arms or jaws of the U-shaped fastener body, the arms spring apart to release the fabric.

Moreover, none of the above patents disclose a surgical staple having two sets of prongs disposed at acute angles to each other for insertion into the patient's skin on opposite sides of the wound or incision, with one of the prongs being directed outwardly toward the edges of the wound.

SUMMARY OF THE INVENTION

It is therefore an object of this invention to provide a surgical staple capable of being emplaced transversely of a wound or incision with a conventional surgical staple applicator in such a manner that the edges of the cut in the skin will be held flush, without slippage or rotation of the staple about the wound or incision.

The surgical staple made in accordance with this invention includes an elongated straight bridge portion in the form of an elongated wire having opposite ends from which depend, preferably at right angles, a pair of opposed anchor prongs. Also projecting from the ends of the bridge portion of the staple, are a pair of converging positioning prongs disposed in the same plane as the anchor prongs and preferably at acute angles to the anchor prongs.

In the emplacement of the surgical staple in the skin for securing the edges of a wound or an incision, the bridge portion is bent by the die and anvil of the conventional applicator in the same manner as a conventional surgical staple, to force both sets of prongs downward in an arc, and laterally inward into the everted portion of the skin on both sides of the wound or incision. As the prongs are forced into the everted portion of the skin, the anchor prongs function in a manner similar to the single set of prongs in a conventional surgical staple, that is to anchor the staple through the skin area on opposite sides of the wound. On the other hand, the other set of positioning prongs are urged inward and upward toward the cut edges of the incision. In their final operative position, the positioning prongs lie close to each other and to the cut edges of the incision to hold the cut edges flush against each other. The staple is also stabilized against rotation about the incision by the penetration of 4 prongs instead of 2 within the skin area surrounding the incision.

Moreover, as the diverging pairs of anchor and positioning prongs move through the skin, they tend to force together the area of the skin caught between the adjacent prongs, as well as forcing the portion of the skin between the opposing prongs together, to reduce hemorrhage and pain, and to hold the cut edges substantially flush with each other to facilitate and expedite healing with a minimum of scarring.

BRIEF DESCRIPTION OF THE DRAWINGS

FIG. 1 is a top perspective view of a surgical staple made in accordance with this invention;

FIG. 2 is a top perspective view of the same surgical staple disclosed in FIG. 1, but bent into its operative position for securing together the cut edges of a wound or incision;

FIG. 3 is a sectional elevation of the head of a conventional surgical staple applicator in an initial position preparatory to forming the staple made in accordance with this invention, for insertion into an everted skin area on opposite sides of an incision;

FIG. 4 is a view similar to FIG. 3 in which the staple is in an intermediate bent position before emplacement within the skin area;

FIG. 5 is a view similar to FIG. 4 in which the emplacement of the staple within the skin area has been completed;

FIG. 6 is a side elevational view of the surgical staple, made in accordance with this invention, in its operative position within the skin area disclosed in section, closing the incision, with the applicator removed;

FIG. 7 is a cross-sectional elevation of the cut edges of the skin, secured together by a conventional surgical staple, with the surgical staple disclosed in its operative position for securing the incision; and FIG. 8 is a sectional elevation similar to FIG. 7, but disclosing the same conventional surgical staple rotated, with the cut edges of the incision offset.

DESCRIPTION OF THE PREFERRED EMBODIMENTS

Referring now to the drawings in more detail, FIG. 1 discloses a surgical staple 10 made in accordance with this invention. The staple 10 includes an elongated straight bridge or central portion 11 having opposite ends 12 and 13, from which project or depend a pair of opposite anchor prongs 14 and 15 having sharp tips or points 16 and 17. The elongated bridge portion 11 and the depending prongs 14 and 15 all lie in the same plane, and may all be formed integrally from a single piece of wire, or thin rod material, having a uniform cross-section of any desired shape, such as circular.

Projecting toward each other integrally from the bridge portion 11, are a pair of opposed positioning prongs 18 and 19 having sharp pointed tips 20 and 21 which are spaced closer to each other than the tips 16 and 17 of the anchor prongs 14 and 15.

As disclosed in FIG. 1, the positioning prongs 18 and 19, are slightly longer than the anchor prongs 14 and 15, but each of the prongs 14, 15, 18 and 19, is substantially shorter than the overall length of the bridge portion 11.

Each of the prongs 14, 15, 18 and 19, is preferably straight and all of the prongs 14, 15, 18 and 19, lie substantially in the same plane as the bridge portion 11, and on the same inner side of the bridge portion 11.

The positioning prongs 18 and 19, are preferably integrally joined to the end portions 12 and 13 of the bridge portion 11, each at substantially the same acute angle to its corresponding anchor prong 14 and 15, such as the angle $\theta$ illustrated in FIG. 3. The angle $\theta$ may range 30°–60°, but is preferably approximately 45°.

The positioning prongs 18 and 19 are preferably of the same wire stock as the prongs 14 and 15 and the bridge portion 11, and may be welded, or otherwise joined, to the end portions or junctions 12 and 13 of the staple 10.

The bridge portion 11 is relatively rigid, but is bendable or deformable by the head 22 of a conventional surgical staple applicator, or applicator tool. The head 22 includes a conventional anvil 23 about which the bridge portion 11 is formed, and a conventional die 24 for bending the bridge portion 11 about the anvil 23.

The conventional applicator head 22 is adapted to form the staple 10 into its operative position disclosed in FIG. 2, in such a manner that it will secure the cut edges 27 and 28 of a wound or incision 29 within the skin 30 of a patient, having underlying tissue 31.

The operating sequence of the applicator head 22 upon the staple 10 for securing the cut edges 27 and 28 of the incision 29, is disclosed in FIGS. 3, 4 and 5.

In the loaded position of the staple 10 within the applicator head 22, as disclosed in FIG. 3, the bridge portion 11, lies straight across the anvil 23 with the prongs 14, 15, 18 and 19, depending downward toward the skin 30. The anvil 23 is then centered over the incision 29 so that the bridge portion 11 transversely spans the incision 29, preferably symmetrically about the incision 29, with the opposed prongs 14, 18 and 15, 19 on opposite sides of the incision 29.

The skin 30 is maintained in a mounded or upward everted position, as disclosed in FIG. 3, by surgical forceps, not shown, to facilitate penetration of the prongs 14, 15, 18 and 19 through the upstanding portions of the skin 30 on opposite sides of the incision 29.

The applicator is then manipulated to cause the die 24 to descend against the bridge portion 11 on opposite sides of the anvil 23 to form a pair of bends 32 and 33, preferably symmetrically about the center of the bridge portion (FIG. 4). Continued descent of the die 24, deforms the bridge portion 11 about the bends 32 and 33, until the pointed tips 16, 20, 21 and 17, penetrate the upstanding portions of the skin 30 and are forced through the skin 30 into the underlying tissue 31. The die 24 continues to descend until it reaches its lowermost position, as disclosed in FIG. 5, in which leg portions 34 and 35 of the bridge portion 11, are formed at right angles to the main portion of the bridge portion 11 and parallel to each other about the bends 32 an 33, as illustrated in FIGS. 2, 5 and 6.

When the leg portions 34 and 35 are at substantial right angles to the main part of the bridge portion 11, the anchor prongs 14 and 18 and 15 and 19 are urged to their operative positions disclosed in FIGS. 5 and 6, in which the tips 20 and 21 of the positioning prongs 18 and 19 have been moved upward toward the cut edges 27 and 28, to thereby urge the cut edges 27 and 28 substantially flush together. The movement of the tips 20 and 16, and 21 and 17 toward each other on opposite sides of the incision 29, tends to force the opposing faces of the incision 29 together to compress the abutting edges of the incision to improve the healing process.

Furthermore, as the diverging prongs 14 and 18 on one side of the incision 29, and the diverging prongs 15 and 19 on the opposite side of the incision 29, force their way through the opposite portions of the skin 30, they tend to compress and squeeze the portions of the skin 30 and tissue 31 between the prongs 14–18 and 15–19 together to close the capillary blood vessels 38 within the compressed tissue 31 (FIG. 5) and minimize hemorrhaging or bleeding.

As disclosed in FIG. 6, the main portion of the bridge portion 11 is spaced above the skin 30 to minimize edema and to provide sufficient space above the skin 30 for removal of the staple 10 by a suitable conventional staple removing tool.

As illustrated in FIG. 6, the length of the respective prongs 14, 18, 15 and 19 are such that their tips 16, 20, 17 and 21 do not touch each other when the staple is in operative position, nor do they penetrate the plane of the incision 29.

Also, the number, that is four, prongs 14, 15, 18 and 19, as well as the vertical spacing and angularity of the positioning prongs 18 and 19 from the anchor prongs 14 and 15, provide sufficient stability to the staple 10 to hold the cut edges 27 and 28 in snug and flush engagement with each other, as disclosed in FIG. 5, to prevent rotation of the staple 10 in the transverse plane of the incision 29, as well as to eliminate relative movement between the edges of the skin 27 and 28.

FIG. 7 illustrates a conventional surgical staple 40 having an elongated central portion 41 joints 42 and 43 and depending anchor prongs 44 and 45 having sharpened tips 46 and 47 respectively. The conventional surgical staple 40 is disclosed in FIGS. 7 and 8 after it has been deformed about the bends 48 and 49 to form the legs 50 and 51 by a staple applicator or applicator tool, such as the applicator tool head 22 illustrated in FIGS. 3–5.

In FIG. 7, the staple 40 is illustrated in its desired deformed operative position symmetrically disposed in an upright position about both sides of the incision 29. If the surgical staple 40 maintains its operative position disclosed in FIGS. 7, then the incision 29 will heal properly. However, in most instances, the staple 40, because it only has a pair of anchor prongs 44 and 45, tends to turn in the transverse plane of the incision 29 to the rotated position of FIG. 8, in which the cut edges 27 and 8 become offset or disaligned to prolong the pain and healing process.

Thus, it is this rotated operative position of a conventional surgical staple 40, as illustrated in FIG. 8, with all the resultant undesirable consequences, which applicant's surgical staple 10 is designed to overcome.

What is claimed is:

1. A surgical staple adapted to be deformed and emplaced in human skin by a surgical staple applicator to join the opposed edges of an incision in the skin of a patient, comprising:
    (a) an elongated straight wire-like bridge portion having an inner side and opposite ends, said bridge portion being adapted to transversely span the opposed edges of an incision with said inner side opposing said incision,
    (b) said wire-like bridge portion being deformable by a staple applicator,
    (c) a pair of wire-like anchor prongs having pointed tips, depending from said inner side and from the corresponding opposite ends of said bridge portion and disposed in substantially the same plane as said bridge portion, each of said anchor prongs being substantially of uniform cross-section and shorter than said bridge portion and being adapted to penetrate the skin on opposite sides of the incision, when the bridge portion is deformed to an operative incision closing position by the applicator,
    (d) a pair of wire-like positioning prongs of uniform cross-section depending from said inner side of said wire-like bridge portion in substantially the same plane as said anchor prongs, said positioning prongs having pointed tips spaced closer together than the tips of said anchor prongs so that said positioning prongs penetrate the skin substantially closer to the opposed edges of the incision than the anchor prongs to hold the incision edges together and to prevent rotation of said staple in a transverse plane relative to the incision, when said bridge portion has been deformed to said operative position.

2. The invention according to claim 1 in which said positioning prongs are directed toward each other and form acute angles with said bridge portion.

3. The invention according to claim 2 in which said positioning prongs depend from the corresponding opposite ends of said bridge portion.

4. The invention according to claim 3 in which each of said positioning prongs is longer than each of said anchor prongs and adapted to force the closed incision edges together in said operative position.

5. The invention according to claim 4 in which each of said positioning prongs forms an acute angle in the range of 30°–60° with its corresponding anchor prong on the same end of said bridge portion.

6. The invention according to claim 5 in which said acute angle is approximately 45°.

7. The invention according to claim 1 in which said bridge portion is bent in its deformed operative position to have a substantially straight central portion, a pair of leg portions of equal length depending at substantially right angles to the ends of said central portion, and the tips of the corresponding opposed anchor prongs and positioning prongs are spaced apart within the skin of the patient on opposite sides of the incision, in said operative position.

* * * * *